United States Patent
Yamada et al.

(10) Patent No.: US 8,154,722 B2
(45) Date of Patent: Apr. 10, 2012

(54) SENSOR ELEMENT STRUCTURE, SENSOR ELEMENT ARRAY, AND MANUFACTURING METHOD OF SENSOR ELEMENT ARRAY

(75) Inventors: Tomohiro Yamada, Yokohama (JP); Yoichiro Handa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 987 days.

(21) Appl. No.: 11/677,890

(22) Filed: Feb. 22, 2007

(65) Prior Publication Data

US 2007/0206194 A1 Sep. 6, 2007

(30) Foreign Application Priority Data

Mar. 3, 2006 (JP) ................................. 2006-057908

(51) Int. Cl.
*G01J 3/44* (2006.01)
(52) U.S. Cl. ........ 356/301; 356/302; 356/454; 356/519; 422/50; 422/68.1; 422/82.05; 422/83
(58) Field of Classification Search .................. 356/301, 356/454, 519
See application file for complete search history.

(56) References Cited

U.S. PATENT DOCUMENTS

| | | | | |
|---|---|---|---|---|
| 7,359,048 B2 * | 4/2008 | Wang et al. | .................... | 356/301 |
| 7,388,661 B2 * | 6/2008 | Li et al. | .......................... | 356/301 |
| 2003/0059820 A1 * | 3/2003 | Vo-Dinh | ............................ | 435/6 |
| 2003/0132392 A1 | 7/2003 | Kuroda et al. | ................ | 250/397 |
| 2006/0034729 A1 * | 2/2006 | Poponin | ..................... | 422/82.05 |

OTHER PUBLICATIONS

Amanda J. Haes et al, "A Localized Surface Plasmon Resonance Biosensor: First Steps Toward an Assay for Alzheimer's Disease," 4(6) Nano Letters 1029-34 (2004).

* cited by examiner

*Primary Examiner* — In Suk Bullock
*Assistant Examiner* — Robert Eom
(74) *Attorney, Agent, or Firm* — Fitzpatrick, Cella, Harper & Scinto

(57) ABSTRACT

Even when only a few antigens exist in a specimen, a change in a dielectric constant and a change in an optical spectrum accompanied thereto in the periphery of a conductive member are made larger, so that sensing at high sensitivity can be performed. A structure including a protrusion including a dielectric material protruded on a substrate and a conductive member provided on a first surface of the protrusion, in which the maximum value of the cross-sectional area in the cross-section in parallel with a first surface of the conductive member is larger than the area of the first surface.

8 Claims, 7 Drawing Sheets

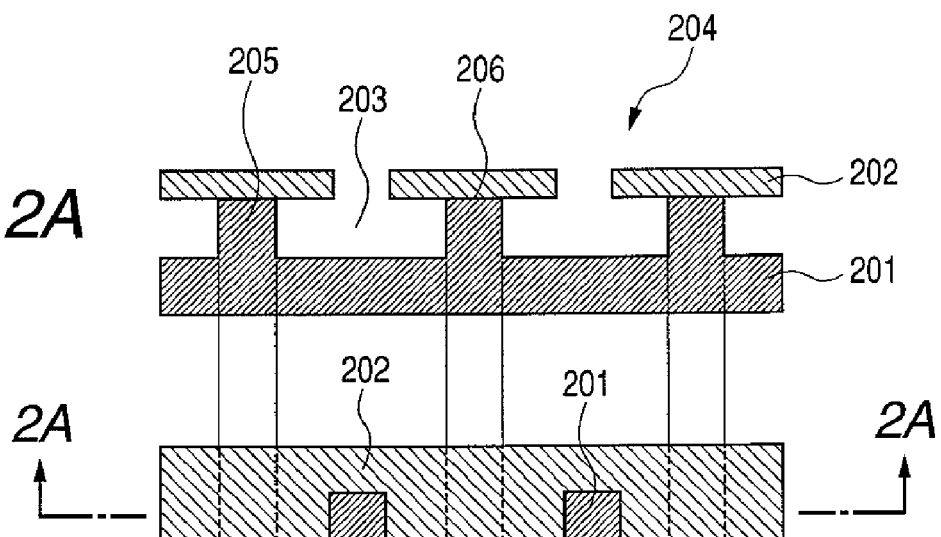
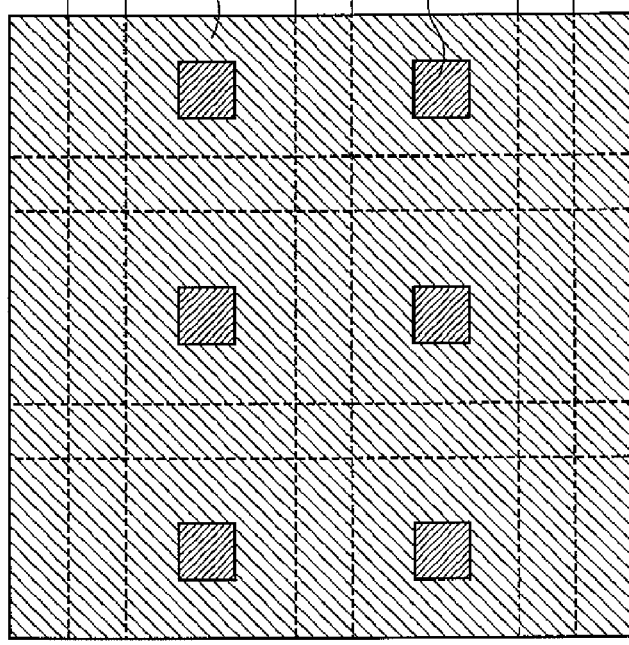

SENSOR ELEMENT STRUCTURE, SENSOR ELEMENT ARRAY, AND MANUFACTURING METHOD OF SENSOR ELEMENT ARRAY

BACKGROUND OF THE INVENTION

1. Field of the Invention

The present invention relates to a sensor element structure, sensor element array, manufacturing method of the sensor element array, and sensing device, which are used in a chemical sensing device and the like.

2. Description of the Related Art

It is generally known that surface Plasmon is induced on a boundary surface between a micro electrically conductive structure and a dielectric material.

This surface Plasmon is known to have a resonance wavelength in response to the structure and change transmitted light, reflected light, and the like from the electrically conductive structure at the resonance time (surface Plasmon resonance).

This surface Plasmon resonance has the resonance conditions decided by a dielectric constant of the periphery of the micro electrically conductive structure. Consequently, the change in the dielectric constant of the periphery of the electrically conductive structure can be detected as a change in the resonance conditions.

Specifically, a change in the resonance conditions can be detected by allowing a light to irradiate and transmit the electrically conductive structure in contact with the dielectric material and measuring a change in optical spectrum.

The surface Plasmon resonance is extremely sensitive to a change in dielectric constant in the periphery of the electrically conductive structure, and this phenomenon is applied to a bio-sensor and the like, thereby realizing a high sensitive sensing.

Hence, the sensing utilizing this surface Plasmon resonance is expected to have a wide range of applications in the fields of medical treatment as well as food, environment, and the like.

For example, when an antigen-antibody reaction is excited in the surface of a metal structure, the antigen-antibody reaction can be detected by using this surface Plasmon resonance.

For example, Richard P. Van Duyne et al (NANO LETTERS, 2004, Vol. 4, No. 6, 1029-1034) disclose the use of a micro Ag thin film fine grain structure formed on a smooth substrate as an electrically conductive thin film structure.

An antigen concentration is measured from a state in which an antibody alone is attached to this structure surface and a change in optical spectrum in a state in which this antibody is further joined with the antigen.

In addition to the above, it is known that a complex of oxygen and substrate, a complementary base pair formation by DNA-DNA hybridization, and the like can be similarly detected.

By the way, as described above, when a change in the dielectric constant in the periphery of the metal structure is detected as a change in optical spectrum by utilizing the surface Plasmon, the change in optical spectrum was small in the conventional configuration.

Hence, a high sensitive sensing has been difficult, and to enable the high sensitive sensing, the increase of change in optical spectrum has been desired.

SUMMARY OF THE INVENTION

The present invention id directed to a sensor element structure, comprising: a protrusion formed on a substrate and protruded from the substrate, and a conductive member located on a first surface of the protrusion and in parallel with the substrate, wherein the maximum of cross-section of the conductive member in parallel with the first surface is larger than the area of the first surface.

The conductive member can comprise a thin film. The conductive member can comprise metal. The conductive member can comprise a semiconductor.

The present invention is directed to a sensor element array, wherein the sensor element structure is periodically plurally disposed.

In the sensor element array, a plurality of conductive members isolated electrically can be periodically disposed.

In the sensor element array, a ratio of the maximum cross-section to the surface area of the first surface can be in the range of not less than 1.01 to not more than 400.

The conductive member can be comprised of a periodical arrangement of a plurality of isolated openings.

In the sensor element array, a ratio of the maximum cross-section to the surface area of the first surface can be in the range of not less than 1.01 to not more than 10.0.

The present invention is directed to a sensing device, comprising: the sensor element array; a reaction well accommodating the sensor element array; a specimen supplying portion and a specimen discharge portion connected to the reaction well through a channel; a light irradiating portion disposed so as to irradiate a light to the array; and a photodetector disposed so as to detect a light from the sensor element array.

The present invention is directed to a manufacturing method of a sensor element array, comprising the steps of: preparing a dielectric material substrate; depositing an electrically conductive material layer on the dielectric material substrate; providing a mask pattern on the electrically conductive material layer; selectively etching mask pattern on the electrically conductive material layer; and etching the mask pattern on the dielectric material substrate.

Further features of the present invention will become apparent from the following description of exemplary embodiments with reference to the attached drawings.

BRIEF DESCRIPTION OF THE DRAWINGS

FIGS. 2A and 2B are schematic diagrams illustrating one example of the sensor element array of the present invention.

DESCRIPTION OF THE EMBODIMENTS

As the results of the intensive studies, the present inventor discovered that the modification of one of a conductive member and dielectric material substrate into a specific structure makes the surface area of the conductive member larger, whereby an antibody can be fixated on the surface of the conductive member in much higher concentration. As a result, the inventor discovered that sensing at high sensitivity can be performed.

That is, the sensor element structure of the present invention is modified into the conductive member having a specific structure, whereby the antibody fixated on the surface of the conductive member is given high concentration, and more antibody reactions are allowed to be performed on the surface of the conductive member.

In the present invention, as a result, even when the antibody exists in a specimen in a small quantity only, a change in the dielectric constant in the periphery of the conductive member and a change in optical spectrum accompanied with this change are made larger, so that sensing with high sensitivity can be performed.

A sensor element structure of the present invention is a sensor element structure, comprising: a protrusion formed on a substrate surface and protruding from the substrate surface; and a conductive member located on a first surface in parallel with the substrate surface of the protrusion; wherein the maximum value of a cross-sectional area when the conductive member is cut off at a plane in parallel with the first surface is larger than the area of the first surface.

In the present invention, the conductive member may comprise a thin film.

Further, in the present invention, the conductive member may be made of one of metal and semiconductor.

Incidentally, in the present specification, the material comprising the [conductive member] also includes not a full electric conductor such as a semiconductor, but the material slightly higher in electric resistance value, as compared with the electric conductor.

By the sensor element structure and sensor element array of the present invention, the change in the dielectric constant generated in the periphery of a microstructure can be optically detected with good sensitivity. Further, by using the sensing device of the present invention, highly sensitive chemical sensing can be performed.

Further, by a manufacturing method of the sensor element array of the present invention, these micro structure arrays can be manufactured with good precision and by a simple process.

(Sensor Element Structure and Array)

Figure 1A:
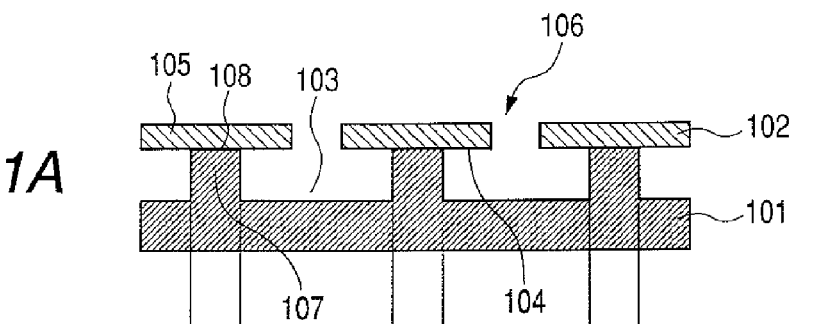
FIGS. 1A and 1B are schematic diagrams illustrating one example of a sensor element array of the present invention.
Figure 1B:
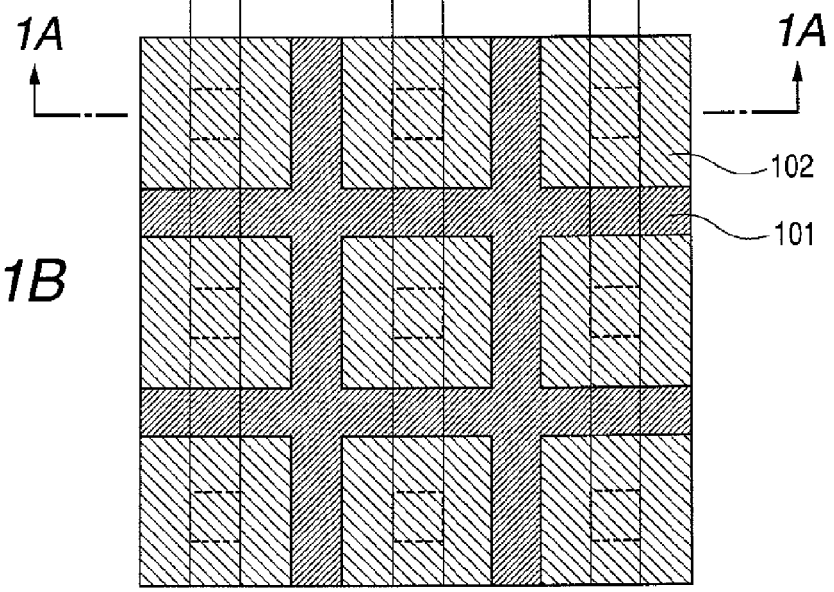

FIGS. 1A and 1B are views illustrating the outline of one example of the embodiment of the present invention. FIG. 1B is a top view of the sensor element array of the present invention, and FIG. 1A represents a cross-sectional view cut along the line 1A-1A of the sensor element array of FIG. 1B.

In the present embodiment, a protrusion 107 is protruded from the surface of a substrate 101 (for example, dielectric material), and on a first surface 108 in parallel with the surface of the substrate 101 of this protrusion 107, a micro electrically conductive structure (conductive member) 102 is disposed.

The maximum value of the cross-sectional area (area of the portion representing the conductive member of FIG. 1B) in a cross section in parallel with the first surface 108 of the conductive member 102 is larger than the area (portion surrounded by a dotted line of FIG. 1B) of the first surface 108.

Here, as an example, the dielectric material substrate 101 and the protrusion are made of quartz 107 and the conductive member 102 is microdot-shaped and is made of Au.

Here, an upper surface 105 and an under surface 104 of the conductive member 102 comprise thin films having equal areas. However, shown here is one example, and the present invention of the patent application is not limited in the shape of the conductive member.

Figure 9A:
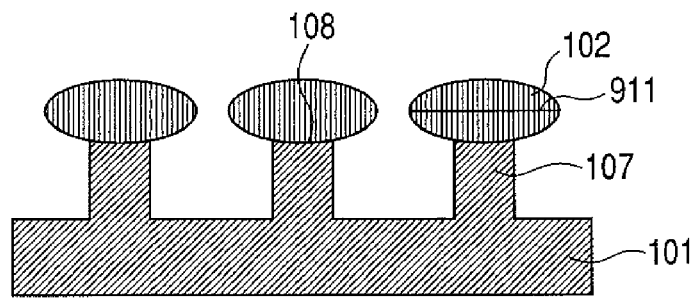
FIGS. 9A and 9B are schematic diagrams illustrating one example of the sensor element structure and the sensor element array of the present invention.
Figure 9B:
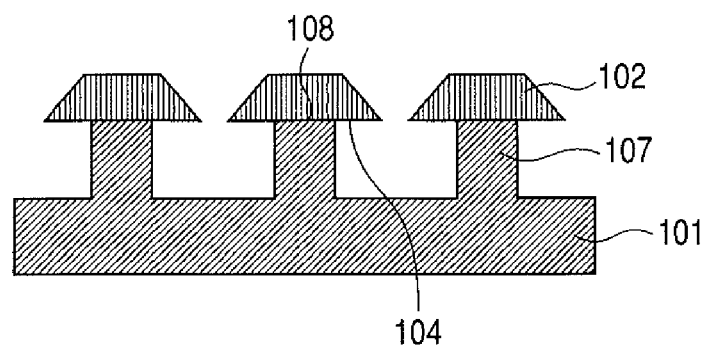

For example, shown in FIG. 9A is an oval disc shaped example as the conductive member 102, and in FIG. 9B is shown a trapezoidal example.

That the maximum value of the cross-sectional area when the conductive member is cut off by the surface in parallel with the first surface as referred to by the present invention is larger than the area of the first surface means that the maximum value of the cross-sectional area in a plane in parallel with the first surface 108 of the conductive member 102 is larger than the area of the first surface 108.

In FIG. 9A, the cross-sectional area in 911 of an oval is the maximum value of the cross-sectional area. In FIG. 9B, the under surface 104 of the conductive member 102 indicates the maximum value of the cross-sectional area.

In the ordinary case, as shown in FIG. 1A, the conductive member 102 is thin-film shaped, and its upper surface 105 and under surface 104 have the same area. In that case, the maximum value of the cross-sectional area is identical with the area of the upper surface 105.

In the sensor element structure of the present invention, the maximum value of the cross-sectional area of the conductive member 102 is made larger than the area of the surface 108 of the protrusion 107, so that the surface area of the conductive member 102 is made larger, thereby making an area to seize a detection target matter larger.

The substrate 101 preferably uses a material high in transmitivity for the wavelength of measuring beams of optical spectrum, and the dielectric material is cited as a desirable example. However, it is not that the substrate 101 is particularly limited to this material. Further, the substrate and the protrusion may be made of the same material or different material, but may preferably be made of the same material.

The electrically conductive material (micro electrically conductive structure) 102 can use a material such as metal and semiconductor. In case of using metal, the materials little in dielectric loss such as Au, Ag, Cu and Al can be used, but the materials are not particularly limited to these materials.

Figure 1C:
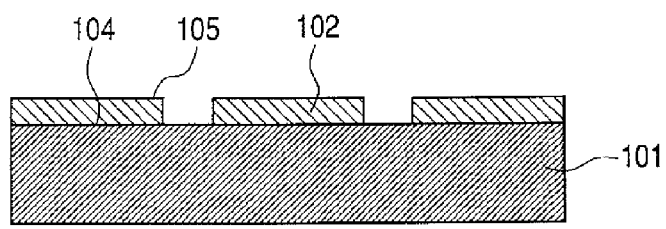
FIG. 1C is a schematic diagram showing one example of a conventional sensor element array.

In this micro structure array, since the protrusion 107 is protruded from the dielectric material substrate 101, a concave portion 103, for example, is formed between the protrusions 107 similarly to FIGS. 1A, 1B and 1C.

The maximum values of the existence of this concave portion 103 and the cross-sectional area of the conductive member (micro electrically conductive structure) 102 are larger than the area of the first surface 108, so that a great majority of the under surface portion 104 on the dielectric material substrate side of the conductive member 102 is exposed. As a result, the area to seize the detection target matter is increased.

The height (length in the normal direction of the substrate) of the protrusion 107 is preferably not less than 10 nm and not more than 500 nm, and more preferably not less than 20 nm and not more than 100 nm. Since the height of the protrusion is within these ranges, an antibody and antigen of a typical size can develop an antigen-antibody reaction in the under surface 104.

Further, in the upper surface and under surface of the micro electrically conductive structure (conductive member), the specimen can be effectively detected, and an element fabrication can be further easy.

The shape of the micro electrically conductive structure (conductive member) is not particularly limited if the maximum value of the cross-sectional area in the cross-section in parallel with the first surface is larger than the area of the first surface.

The cross-sectional area of the cross-section in parallel with the first surface of the micro electrically conductive structure may or may not change for the normal direction of the first surface.

When the cross-sectional area does not change for the normal direction of the first surface, in the cross-section in parallel with the first surface of the micro electrically conductive structure, whichever cross-section it is, it has the same shape and size.

The micro electrically conductive structure can be thin film-shaped. By making it thin film-shaped, the surface of the micro electrically conductive structure can be smooth, and at the same time, the surface area of the micro electrically conductive structure can be larger. Hence, the change in the dielectric constant of the periphery of the micro electrically conductive structure can be detected with high sensitivity.

As the shape of the cross section in parallel with the first surface of the micro electrically conductive structure, a circular form, oval form, square form, rectangular form, polygonal form and other graphic forms comprising straight lines and curved lines can be cited. However, the shape is not particularly limited to these forms.

Looking from the normal direction of the first surface, the center of gravity of the first surface and the center of gravity of the cross-section of the micro electrically conductive structure may or may not be aligned.

The size and shape of the first surface which is a surface in contact with the micro electrically conductive structure of the protrusion are not particularly limited. As the shape of the first surface, for example, circular form, oval form, square form, rectangular form, polygonal form and other graphic forms comprising straight lines and curved lines can be cited.

The first surface may be or may not be in parallel with the substrate. When the first surface is not in parallel with the substrate, for example, a mode of allowing the first surface to incline so as to have a predetermined angle with the substrate can be cited.

However, from a view point of workability and uniformity of the first surface, the first surface is preferably in parallel with the substrate.

In the present invention, this micro structure (conductive member) comprising the protrusion and the micro electrically conductive structure can be made into a micro structure array disposed in a desired dot array shape.

Here, the "dot array shape" means that a plurality of isolated micro structures (conductive members) is disposed with a certain periodicity in the in-plane direction. Hence, for example, when the periodicity is a tetragonal lattice arrangement, in case the dot array shape is looked from the upper surface, the dielectric material substrate looks like a lattice (FIG. 1B).

When the conductive member is disposed in this dot array shape, s ratio S2/S1 of an area S1 of the first surface to the maximum value S2 of the cross-section area when cut off by a plane in parallel with the first surface of the conductive member can be not less than 4 and not more than 400.

Further, in the present invention, the conductive member periodically disposed with a plurality of isolated openings can be also used. This type is referred to as a hole-array shape.

When the conductive member of this type is used, the ratio S2/S1 of the area S1 of the first surface to the maximum value S2 of the cross-sectional area when cut off by a plane in parallel with the first surface of the conductive member can be not less than 1.01 and not more than 10.0.

(Manufacturing Method of Micro Structure Array)

Such micro structure array can be manufactured in such a manner that an electrically conductive material is deposited on a substrate, and after that, it is subjected to patterning, and then, based on this patterning, the substrate is etched. As an example, the following can be cited, which is the manufacturing method comprising the steps of:

(1) preparing a dielectric material substrate,
(2) depositing a conductive member material on the dielectric material substrate,
(3) providing a mask pattern on the conductive member material,
(4) performing an etching on the conductive member material with the mask pattern as a mask, and making the conductive member material into the conductive member
(5) performing an isotropic etching on the dielectric material substrate with the mask pattern as a mask, and
(6) removing the mask pattern.

More specifically, a method of fabricating the dot array is described as follows.

For example, an Au thin film is provided on a dielectric material substrate (the above described steps (1) and (2)), and after that, a resist pattern is prepared by the EB drawing technique (the above described step (3)).

After that, a method of using the resist pattern for the mask and performing dry etching on the Au thin film can be cited (the above described step (4)).

Further, after these steps, by using the resist patter for the mask, the isotropic etching is performed on the quartz substrate by F system gas (the above described step (5)) or the quartz substrate is dipped in an $SiO_2$ erosive chemical such as KOH.

By such method, similarly to FIG. 1A, a shape having the under surface 104 exposed can be fabricated.

In addition to the above described method, a method can be cited such as, after a resist layer is formed on a quartz substrate, forming a resist pattern on a quartz substrate by the EB drawing technique and forming an Au thin film on this pattern, and after that, removing the resist pattern, thereby performing a lift-off method.

Incidentally, in a state in which the dots of the conductive member are simply formed on the smooth substrate, a configuration is made such as shown in FIG. 1C, and the under surface portion 104 of the conductive member is not exposed, so that the surface area of the conductive member is small.

Consequently, in the conductive member having such a configuration, the change in optical spectrum by detection of the measured object becomes small, and the sensitivity is reduced.

On the other hand, in the micro structure of the present invention, the maximum value of the cross-sectional area in the cross-section in parallel with the first surface of the conductive member is larger than the area of the first surface, and the under surface portion is exposed similarly to FIG. 1A.

Hence, the surface area of the conductive member is large, and the change in optical spectrum by the detection of the measured object is large, so that the sensitivity can be increased.

Incidentally, in FIG. 1A, while a description was made with the micro structure array as the dot array, the layout mode of the micro structure in the micro structure array is not limited to this.

For example, the lay out mode may be a hole array structure. FIG. 2B is a top view of one example of the micro structure array of this hole array structure. FIG. 2A is a sectional view cut along the line 2A-2A of one example of the micro structure array of FIG. 2B.

This hole array structure is a structure in which a plurality of openings is disposed with periodicity in the in-plane direction (FIGS. 2A and 2B).

That is, the protruding portion is periodically formed on the substrate, and on this protrusion, a plurality of conductive members is provided.

The conductive member provided on each protrusion comprises the conductive members comprising the same surfaces with adjacent conductive members mutually communicated (connected) with each other.

This micro structure array is periodically disposed with a concave portion (exposed micro opening) 203.

Figure 3A:
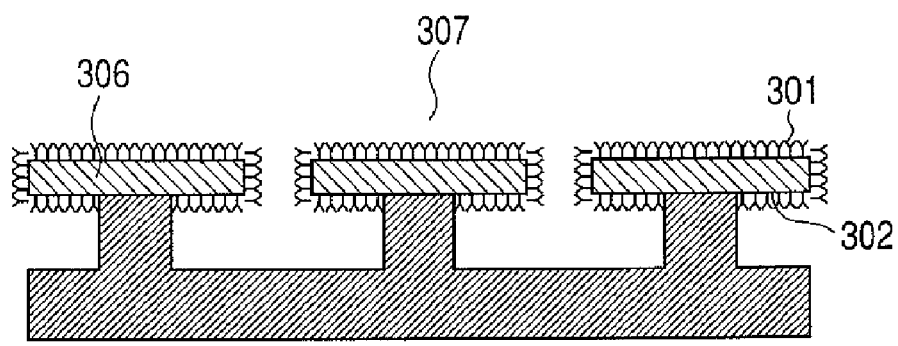
FIGS. 3A, 3B and 3C are schematic diagrams describing the detection process of an antigen by the sensor element array of the present invention.

Here, consider an example in which the micro structure 307, for example, is used for biosensing. When a micro electrically conductive structure 306 of the present invention is modified by an antibody, as shown in FIG. 3A, a great majority of the under surface portion 302 is put into a state in which it is modified by an antibody 301.

First, the optical spectrum 304 (spectrum 1) in this state is measured.

Next, an antigen 302 is let flow in the vicinity of the micro structure 307, and an antigen 303 is allowed to be seized by the micro electrically conductive structure 306, and after that, a specimen is discharged, and is cleansed by a phosphate buffer solution and the like, and once again, an optical spectrum 305 (spectrum 2) is measured.

Figure 3B:
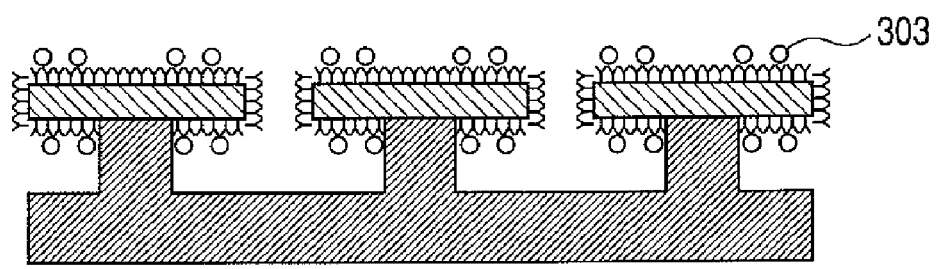

At the second time measurement of the optical spectrum, according to the antigen concentration, an antigen-antibody reaction develops with the antibody on the surface of the micro electrically conductive structure 306, and as a result, similarly to FIG. 3B, part of the antibody is put into a combined state with the antigen 303.

Here, the case where only the antibody exists on the surface of the micro electrically conductive structure 306 and the case where the antibody is further combined with the antigen are different in the dielectric constant of the periphery of the micro electrically conductive structure 306.

Figure 3C:
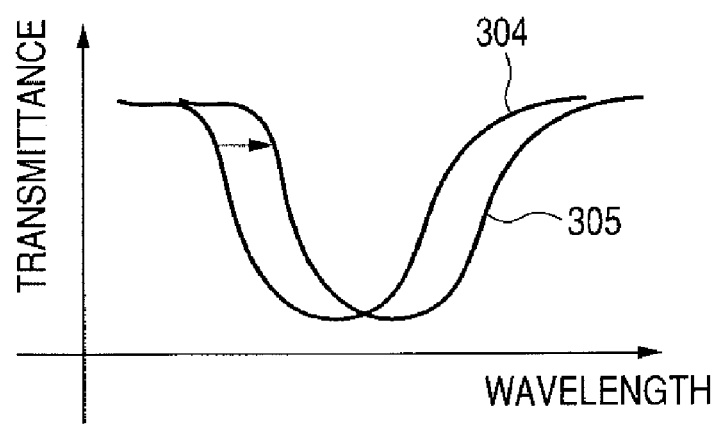

Hence, the resonance conditions of the surface Plasmon change with the result that the optical spectrum 2 in a state after developing the antigen-antibody reaction is different from the optical spectrum 1 (FIG. 3C).

The density in which this antibody-antigen reaction develops depends on the concentration of the antigen, and lower the concentration of the antigen is, smaller the difference between the optical spectrum 1 and the optical spectrum 2 is.

The concentration of the antigen is determined by measuring the difference between the optical spectrums 1 and 2, but in order to measure much lower concentration of the antigen, the change in the optical spectrum before and after the development of the antigen-antibody reaction is preferably great.

In the structural example of the present invention, as compared with the structure of FIG. 1C, the under surface portion 302 is exposed. Hence, even when the structure of the micro electrically conductive structure 306 remains the same, the surface area capable of getting a sense of the change in the dielectric constant of the surface of the structure increases.

That is, in this example, as compared with the structure of FIG. 1C, the development of the antigen-antibody reaction causes a great change in the dielectric constant on the surface of the structure.

Thus, the change in the optical spectrum in the micro structure of the present invention is great because the surface area of the structure per unit volume in which the change in the dielectric constant occurs is increased.

In the micro structure similarly to FIG. 1C, since the upper surface portion 110 is fully exposed, it is in a state in which the antigen-antibody reaction develops, while the under surface portion 104 is in contact with the dielectric material substrate 101.

Hence, this portion is unable to get a sense of the change in the dielectric constant due to chemical modification such as the antigen-antibody reaction developed on the surface of the micro electrically conductive structure 102, and always gets a sense of the dielectric constant of the dielectric material substrate 101.

Hence, in the micro structure similarly to FIG. 1C, usually a sensible change in the dielectric constant is different for the under surface 104 and the upper surface 110, and this leads to restriction of an effective Plasmon excitation in the micro electrically conductive structure 102.

While, in the micro structure of the present invention, since a great majority of the under surface portion 104 is exposed, the dielectric constant of the surface of the micro electrically conductive structure 102 sensible by the upper surface portion 110 and the effective dielectric constant sensible by the under surface portion 104 draw near.

Hence, the exciting conditions of the Plasmon in the upper surface and the under surface of the micro electrically conductive structure 102 draw near, and the Plasmon can be effectively excited.

The relationship between the magnitude of the change in optical spectrum and the concentration of the measured specimen is determined by the specimen, of which concentration is known in advance, so that the concentration of the specimen, of which concentration is unknown, can be decided.

EXAMPLES

First Example

Biosensing

Figure 4A:
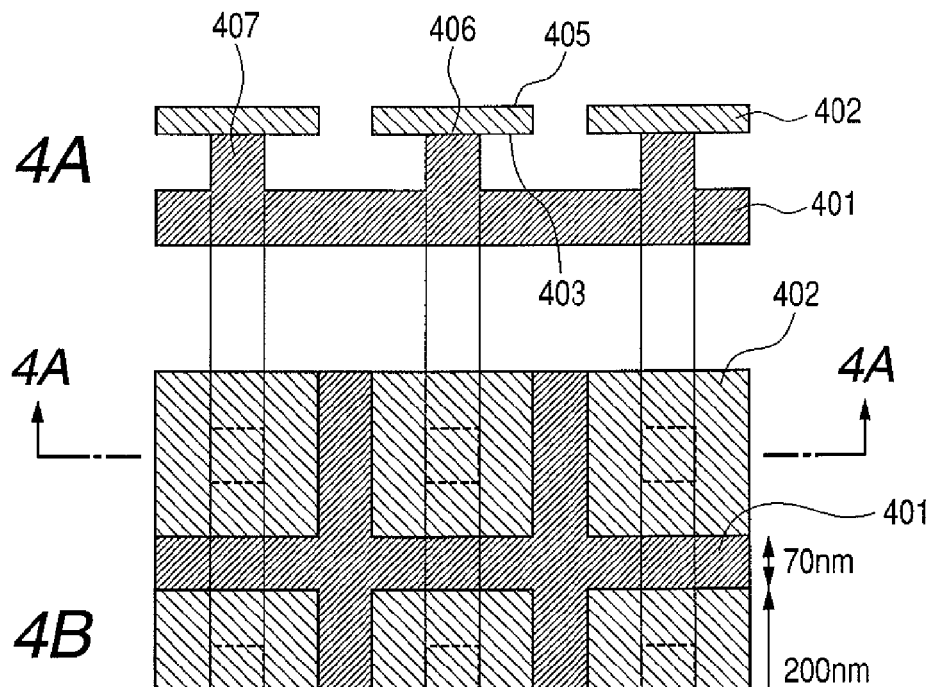
FIGS. 4A, 4B and 4C are schematic diagrams illustrating the sensor element array of a first example.
Figure 4B:
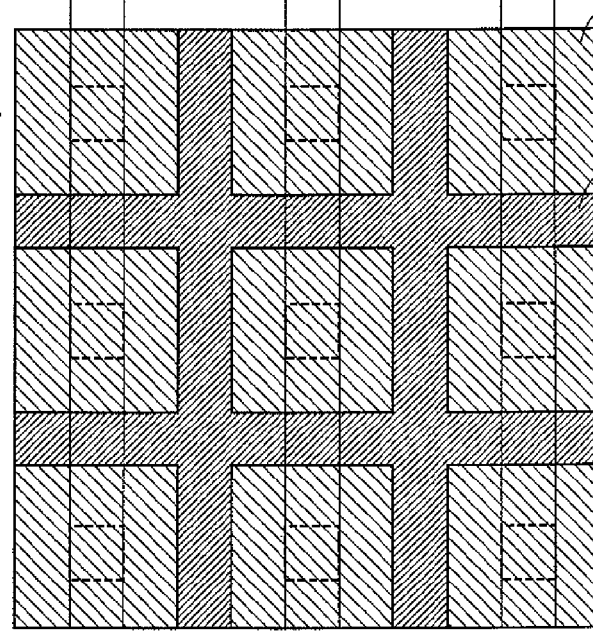
Figure 4C:
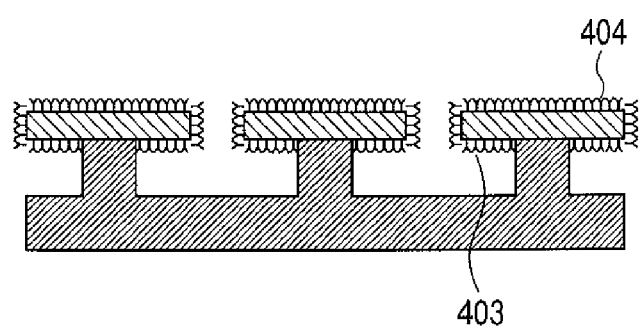

A first structural example of the micro structure of the present invention will be shown in FIGS. 4A, 4B and 4C.

First, a dielectric material substrate was prepared, and an Au thin film was formed. The dielectric material substrate was a quartz substrate of 0.5 mm in thickness, and on this substrate, the Au thin film of approximately 20 nm in thickness was formed. The thickness of the quartz substrate and the Au thin film is not limited to them.

In the present example, while Au was used as an electrically conductive material serving as a micro electrically conductive structure (conductive member), the electrically conductive material is not limited to this only. The electrically conductive material little in dielectric loss such as Ag, Cu and Al can be used. Though the substrate of a ground is not limited to quartz, the matter high in transmitivity for the wavelength used for the measurement of absorption spectrum can be used.

Next, a resist pattern was formed on this Au thin film by an electron beam lithography system. After that, the resist pattern was subjected to dry etching by Ar plasma by using the mask.

As a result, a micro electrically conductive structure 402 having a square form of approximately 200 nm per one side as shown in FIGS. 4A and 4B and disposed in a square lattice pattern at intervals of 70 nm was formed in a dot array form. FIG. 4A is a sectional view cut along the line 4A-4A of FIG. 4B.

After this process, an isotropicetching was performed on the quartz substrate by $CF_4$ plasma.

As a result, a dielectric material substrate 401 existing below the micro electrically conductive structure 402 was also etched, so that the under surface 403 of the micro electrically conductive structure 402 was exposed. Next, the surface of the micro electrically conductive structure 402 was modified by an antibody.

For example, fixation of the micro electrically conductive structure 402 of an anti-AFP (α-fetoprotein) antibody on the Au surface as the antibody can be performed by the following method.

First, an ethanol solution of 11-Mercaptoundecanoic acid having a thiol group is dripped on the micro electrically conductive structure by a spotter and the like, so that a carboxyl group is exposed on the surface of the micro electrically conductive structure.

Next, N-Hydroxysulfosuccinimide water solution and 1-Ethyl-3-[3-dimethylamino]propyl carbodiimide hydrochloride water solution are similarly dripped on the reaction area by the spotter and the like.

As a result, a succinimide group is exposed on the surface of the micro electrically conductive structure.

After that, streptavidin is reacted, and the surface of the micro electrically conductive structure is modified by streptavidin. Then, a biotinylated anti-AFP antibody is fixated on the surface of this micro electrically conductive structure.

In the micro structure of the present invention, similarly to FIG. 4C, the above described under surface portion 403 is also put into a modified state by an antibody 404.

Figure 5:
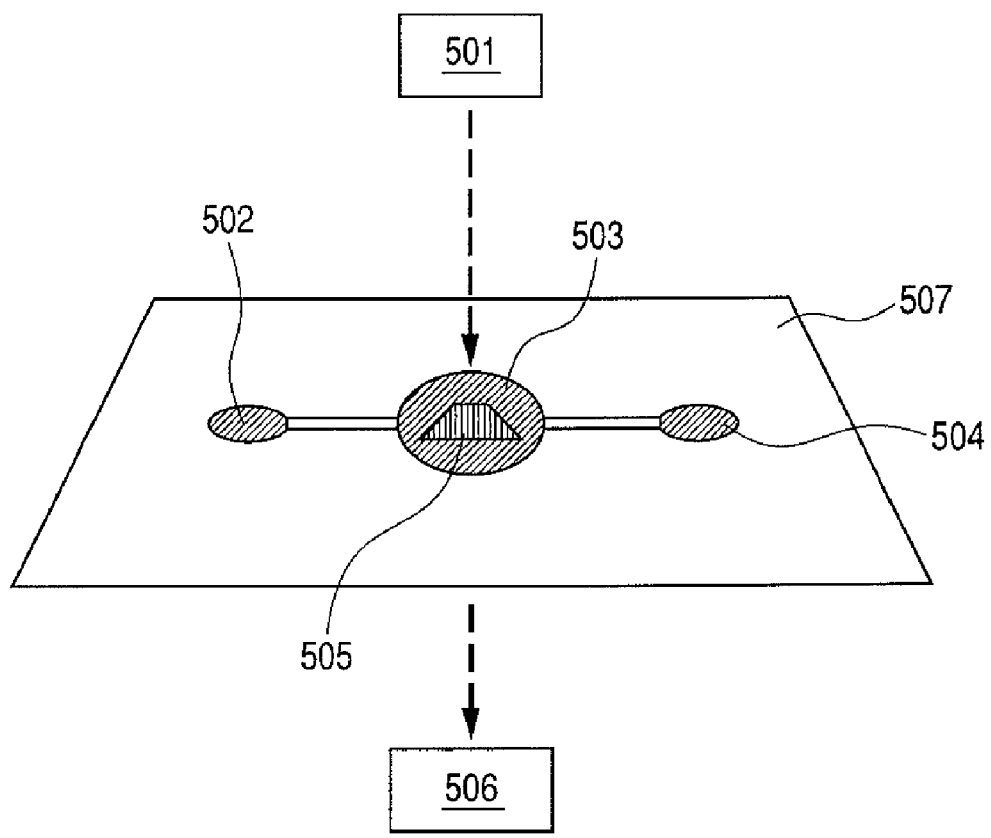
FIG. 5 is a schematic diagram illustrating a sensing device of first and second example.

The measurement of the antigen-antibody reaction and the optical spectrum by using this micro structure is performed in the configuration as shown in FIG. 5.

First, phosphate buffer solution is filled into a reaction well 503, and a light from a light source 501 is irradiated on it, and the transmitted light is detected by a detector 506, thereby measuring an optical spectrum 601 (spectrum 1) of this micro structure 505.

Next, after this phosphate buffer solution is discharged, a specimen containing AFP is injected into the reaction well 503 from an injection port 502, thereby allowing the AFP to be seized by the structure.

After that, the specimen is discharged from a discharge port 504, and the phosphate buffer solution is injected from the injection port 502, and the interior of the reaction well 503 is cleansed. Then, finally, the phosphate buffer solution is filled up.

Next, a light is irradiated from the light source 501, and the transmitted light is detected by the detector 506, so that an optical spectrum 602 (spectrum 2) of this micro structure 505 is measured.

Figure 6:
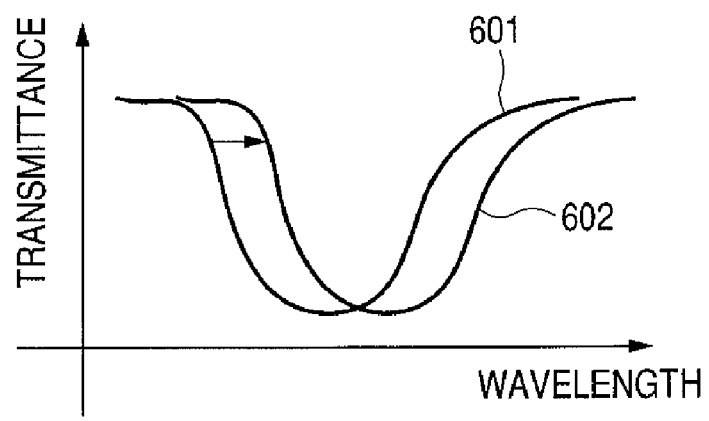
FIG. 6 is a spectrum view representing a surface Plasmon resonance by a sensor element structure of the present invention.

When the optical spectrum 601 (spectrum 1) before and after the antigen-antibody reaction occurs on the surface of the micro electrically conductive structure of this micro structure is compared with the optical spectrum 602 (spectrum 2), the spectrum is shifted by surface Plasmon resonance similarly to FIG. 6.

At this time, the relationship between the shift amount and concentration is determined by using the AFP solution, of which concentration is known in advance, so that the concentration of the measured specimen can be determined.

In this manner, in the micro structure of the present invention, the under surface 403 of the micro electrically conductive structure 402 is exposed, so that the reaction area in which the antigen-antibody reaction occurs is large.

That is, since the area in which the change in the dielectric constant occurs in the surface of the micro electrically conductive structure 402 is large, the change in the optical spectrum before and after the reaction can be larger as compared with the case where the under surface 403 is not exposed.

Further, the great majority of the under surface 403 is exposed similarly to the upper surface 405, so that the effective dielectric constants of the periphery sensible by both surfaces draw near and the Plasmon can be effectively excited.

Further, similarly to the present example, after the thin film layer of the electrically conductive material is formed, it is patterned to a predetermined form, thereby a structure having desired optical characteristics can be fabricated with good reproducibility.

Second Example

Spectrum Measurement

Figure 7A:
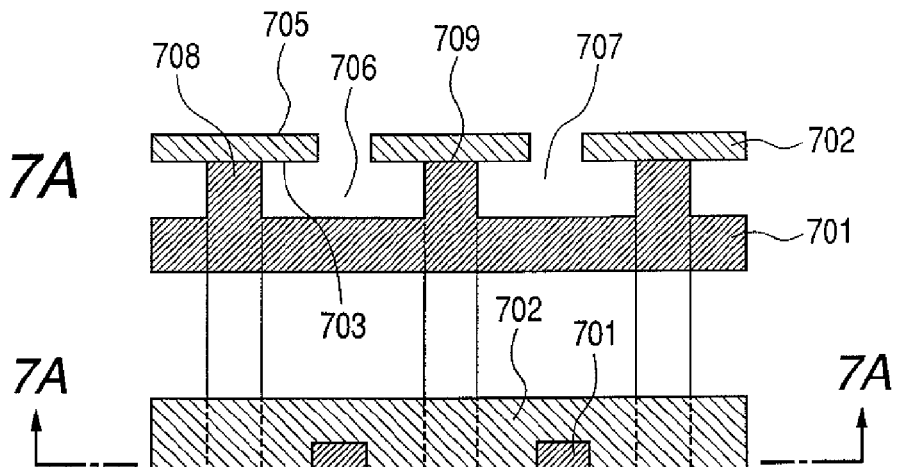
FIGS. 7A, 7B and 7C are schematic diagram illustrating a sensor element array of a second example.
Figure 7B:
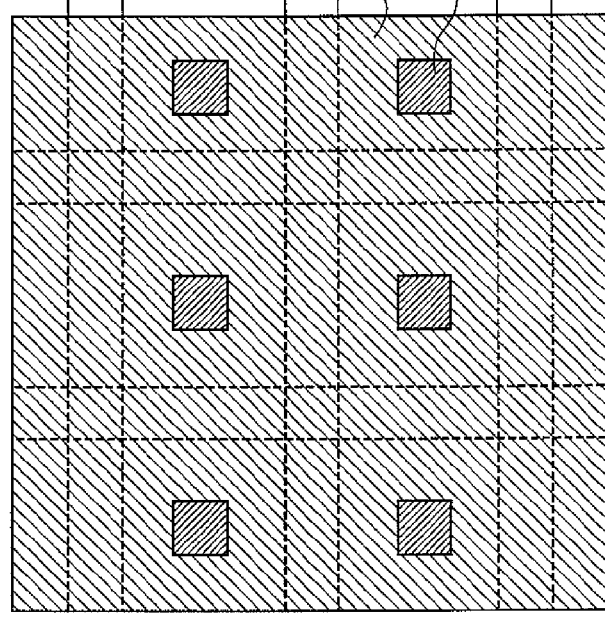
Figure 7C:
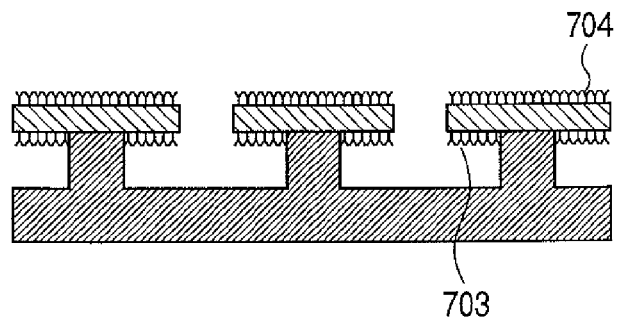

Another structural example of the micro structure of the present invention is shown in FIGS. 7A, 7B and 7C. First, a dielectric material substrate was prepared, and an AU thin film was formed on the substrate.

The dielectric material substrate was a quartz substrate of 0.5 mm in thickness, and on this substrate, the Au thin film of approximately 20 nm in thickness was formed.

Next, as shown in FIGS. 7A and 7B, a micro electrically conductive structure 702 having periodically disposed micro openings was formed in the shape of a hole array.

This method, for example, includes a method in which a resist pattern is prepared on the Au thin film by an EB drawing apparatus, and after that, the Au thin film is dry-etched by dry etching and the like.

After this process, the quartz substrate is subjected to isotropicetching by $CF_4$ plasma.

At this time, a shape (cross-sectional view cut along the line 7A-7A of FIG. 7B) looked from the side surface of the micro electrically conductive structure becomes like FIG. 7A. Next, the surface of the micro electrically conductive structure 702 is modified by an antibody.

For example, when an anti-AFP (α-fetoprotein) antibody is fixated on the Au surface of the micro electrically conductive structure as an antigen, the following method is used.

First, an ethanol solution of 11-Mercaptoundecanoic acid having a thiol group is dripped on the micro electrically conductive structure by a spotter and the like.

As a result, a carboxyl group is exposed on the surface of the micro electrically conductive structure.

Next, N-Hydroxysulfosuccinimide water solution and 1-Ethyl-3-[3-dimethylamino]propyl carbodiimide hydrochloride water solution are similarly dripped on the reaction area by the spotter and the like.

As a result, a succinimide group is exposed on the surface of the micro electrically conductive structure.

After that, streptavidin is reacted, and the surface of the micro electrically conductive structure is modified by streptavidin. Then, a biotinylated anti-AFP antibody is fixated on the surface of this micro electrically conductive structure.

In the micro structure of the present example, since the above described under surface portion 703 is also put into a modified state by an antibody 704 as shown in FIG. 7C, the measurement of the specimen can be performed with high sensitivity.

The measurement of the antigen-antibody reaction and the optical spectrum by using this micro structure is performed in the configuration as shown in FIG. 5.

First, a phosphate buffer solution is filled into a reaction well 503, and a light from a light source 501 is irradiated on it, and the transmitted light is detected by a detector 506, thereby measuring the optical spectrum of this micro structure 505.

Next, after this phosphate buffer solution is discharged, a specimen containing AFP is injected into the reaction well 503 from an injection port 502, thereby allowing the AFP to be seized by the structure.

After that, the specimen is discharged from a discharge port 504, and the phosphate buffer solution is injected from the injection port 502, and the interior of the reaction well 503 is cleansed. Then, finally, the phosphate buffer solution is filled up.

Next, a light is irradiated from the light source 501, and the transmitted light is detected by the detector 506, so that the optical spectrum of this micro structure 505 is measured.

Before and after the antigen-antibody reaction occurs on the surface of the micro electrically conductive structure of this micro structure, the spectrum is shifted by the surface Plasmon resonance similarly to FIG. 6.

At this time, the relationship between the shift amount and concentration is determined by using the AFP solution, of which concentration is known in advance, so that the concentration of the measured specimen can be determined.

In this manner, in the micro structure of the present invention, since the under surface 703 of the micro electrically conductive structure 702 is exposed, the reaction area in which the antigen-antibody reaction occurs is large.

That is, since the area in which the change in the dielectric constant occurs in the surface of the micro electrically conductive structure 702 is large, the change in the optical spectrum before and after the reaction can be larger as compared with the case where the under surface 703 is not exposed.

Further, the great majority of the under surface 703 is exposed similarly to the upper surface 705, so that the effective dielectric constants of the periphery sensible by both surfaces draw near and the Plasmon can be effectively excited.

Further, similarly to the present example, after the thin film layer of the electrically conductive material is formed, it is patterned to a predetermined form, thereby a structure having desired optical characteristics can be fabricated with good reproducibility.

In the case of the common hole array, since a dielectric material substrate 701 blocks one end of an opening portion 706 against the liquid passing through the opening portion 706, the inroad and convection of the liquid are difficult.

However, a concave portion 707 is formed similarly to the hole array of the present invention so that a channel passing through the opening portion 706 and reaching the concave portion is built, and therefore, the inroad and convection of the liquid toward the concave portion 707 becomes easy, and the antigen-antibody reaction can occur on the entire surface of the micro electrically conducive structure 702.

Third Example

Sensing Device

Figure 8:
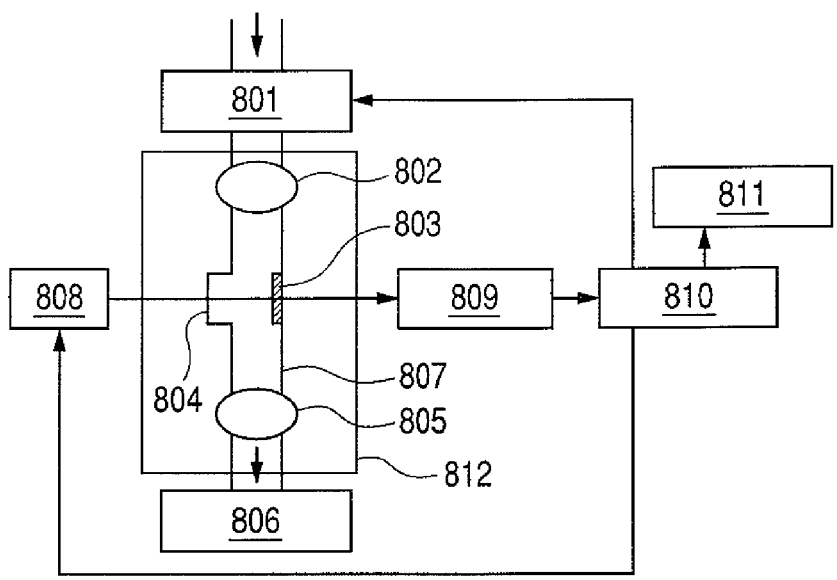
FIG. 8 is a schematic diagram showing a sensing device of a third example.

The present example relates to a sensing device using the micro structure of the present invention. FIG. 8 is a schematic diagram of the sensing device using the micro structure of the present invention.

The sensing device of the present invention mainly comprises a liquid feed pump 801, injection port 802, micro structure array 803, reaction well 804, discharge port 805, waste liquid reservoir 806, channel 807, and substrate 812.

The micro structure array 803 is disposed inside the reaction well 804, and the reaction well 804 is communicated with the injection port 802 and the discharge port 805 through the channel 807.

The liquid feed pump 801 and the injection port 802 comprise a specimen supplying portion, and the waste liquid reservoir 806 and the pump connected thereto as well as the discharge port 805 comprise a specimen discharge port.

The injection port 802 and the discharge port 805 are connected to the liquid feed pump 801 and the waste liquid reservoir 806, respectively.

Driving the liquid feed pump 801 allows a specimen liquid to flow from the injection port 802 to the reaction well 804.

After measuring the specimen liquid, driving a pump (not illustrated) connected to the waste liquid reservoir 806 allows the specimen liquid to flow from the reaction well 804 to the discharge port 805.

On the other hand, this micro structure array 803, before and after detecting the specimen, has the optical spectrum changed by the surface Plasmon resonance.

Hence, to estimate the change in optical characteristics due to the micro structure 803, before and after detecting the specimen, a light is irradiated from a light source (light irradiation portion) 808, and the transmitted light is measured by a spectrophotometer (photodetector) 809.

Further, intensity data per wavelength is led to a central processing unit 810.

The central processing unit 810 allows the measurement result to be displayed on a display unit 811, and at the same time, generates the control signal of the light source unit 808.

By using the micro structure array of the present invention, the sensing device is formed, so that high sensitive sensing (for example, refractive index sensing and biosensing) can be performed.

Further, for further improvement of the observation speed, the micro structure of the present invention is plurally provided, so that a sensing device of the multi-head type may be formed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-057908, filed Mar. 3, 2006, which is hereby incorporated by reference herein in its entirety.

What is claimed is:

1. A sensor element array configured to detect a target substance utilizing plasmon resonance, comprising:
   a plurality of protrusions periodically formed on a substrate surface; and
   a plurality of electrically isolated conductive members disposed on a top surface of the protrusions and in parallel with the substrate surface,
   wherein a maximum of a cross-section of the conductive members in parallel with the top surface is larger than a maximum of a cross-section of the protrusions in parallel with the top surface, and
   wherein a height of the protrusions is not less than 10 nm and not more than 500 nm.

2. The sensor element array according to claim 1, wherein the conductive member comprises a thin film.

3. The sensor element array according to claim 1, wherein the conductive member comprises metal.

4. The sensor element array according to claim 1, wherein the conductive member comprises a semiconductor.

5. A sensing device, comprising:
- a sensor element array according to claim 1;
- a reaction well accommodating the sensor element array;
- a specimen supplying portion and a specimen discharge portion connected to the reaction well through a channel;
- a light irradiating portion disposed so as to irradiate a light to the array; and
- a photodetector disposed so as to detect a light from the sensor element array.

6. The sensor element array according to claim 1, wherein the height of the protrusions is not less than 20 nm and not more than 100 nm.

7. The sensor element array according to claim 1, wherein a part of a surface of the conductive member facing the substrate surface is exposed to air.

8. The sensor element array according to claim 7, wherein the surface of the conductive member facing the substrate surface has an area to capture the target substance.

* * * * *